(12) United States Patent
Gentry et al.

(10) Patent No.: US 7,656,299 B2
(45) Date of Patent: Feb. 2, 2010

(54) BED EXIT AND PATIENT DETECTION SYSTEM

(75) Inventors: Jason M. Gentry, Berkeley, CA (US);
Matthew S. Glei, Honolulu, HI (US);
Rose A. Mills, Alameda, CA (US)

(73) Assignee: Hoana Medical, Inc., Honolulu, HI (US)

( * ) Notice: Subject to any disclaimer, the term of this patent is extended or adjusted under 35 U.S.C. 154(b) by 218 days.

(21) Appl. No.: 11/624,200

(22) Filed: Jan. 17, 2007

(65) Prior Publication Data

US 2008/0169931 A1    Jul. 17, 2008

(51) Int. Cl.
*G08B 23/00* (2006.01)

(52) U.S. Cl. .................. 340/573.1; 340/562; 340/666; 340/686.1; 5/940

(58) Field of Classification Search .............. 340/573.1, 340/5.1, 562, 573.4, 573.5, 664, 666, 686.1; 600/300, 483, 484; 5/618, 624, 940
See application file for complete search history.

(56) References Cited

U.S. PATENT DOCUMENTS

| | | | |
|---|---|---|---|
| 4,175,263 A | 11/1979 | Triplett | |
| 4,365,130 A | 12/1982 | Christensen | |
| 4,539,560 A | 9/1985 | Fleck | |
| 4,633,237 A | 12/1986 | Tucknott | |
| 4,684,767 A | 8/1987 | Phalen | |
| 4,845,323 A | 7/1989 | Beggs | |
| 4,907,845 A | 3/1990 | Wood | |
| 5,144,284 A | 9/1992 | Hammett | |
| 5,184,112 A | 2/1993 | Gusakov | |
| 5,235,319 A | 8/1993 | Hill | |
| 5,253,656 A | 10/1993 | Rincoe | |
| 5,276,432 A | 1/1994 | Travis | |
| 5,353,012 A | 10/1994 | Barham | |

(Continued)

*Primary Examiner*—Toan N Pham
(74) *Attorney, Agent, or Firm*—Fulwider Patton LLP

(57) ABSTRACT

A bed exit and patient detection system especially adapted for use in the general medical or surgical floor area of a hospital or other healthcare facility as part of a vital signs monitoring and remote warning system includes a plurality of pressure sensors disposed in the patient's bed in a series of rectangular strips or zones that run laterally across the bed in the area of the patient's mid-back, hips and mid-legs, respectively. Each zone contains a plurality of sensors, arranged symmetrically about the centerline of the bed, with the corresponding sensors on opposite sides of the centerline in each zone being connected in parallel. The sensors are connected to a processor with multiple input channels that continuously monitors the sensor states to determine, from the pattern of sensor states observed, whether the patient is in bed, out of bed or is actively attempting to exit the bed at the sides or foot of the bed. At least three different sets of bed exit logic rules are available for user selection to configure the system for high, medium or low sensitivity, or bed exit privileges, for any particular patient. In some embodiments, the system also is capable of detecting when a patient is attempting to assume certain prohibited in-bed positions, such as sitting positions or slumping positions. An alarm in the form of a pre-recorded voice announcement or an alarm over a pre-existing nurse call system is provided when the sensor states are indicative of an out-of-bed or an exiting bed condition, or other prohibited in-bed positions, for a predetermined minimum period of time.

35 Claims, 9 Drawing Sheets

U.S. PATENT DOCUMENTS

| | | |
|---|---|---|
| 5,393,935 A | 2/1995 | Hasty |
| 5,429,399 A | 7/1995 | Geringer et al. |
| 5,448,996 A | 9/1995 | Bellin |
| 5,623,760 A | 4/1997 | Newham |
| 5,633,627 A | 5/1997 | Newham |
| 5,844,488 A | 12/1998 | Musick |
| 6,067,019 A * | 5/2000 | Scott ................. 340/573.4 |
| 6,078,261 A | 6/2000 | Davsko |
| 6,133,837 A | 10/2000 | Riley |
| 6,208,250 B1 | 3/2001 | Dixon |
| 6,252,512 B1 * | 6/2001 | Riley ................. 340/665 |
| 6,583,727 B2 | 6/2003 | Nunome |
| 6,696,653 B1 | 2/2004 | Smith |
| 6,727,445 B2 | 4/2004 | Cullinan et al. |
| 6,778,090 B2 | 8/2004 | Newham |
| 6,784,797 B2 | 8/2004 | Smith |
| 6,791,460 B2 * | 9/2004 | Dixon et al. ............. 340/573.1 |
| 6,847,301 B1 | 1/2005 | Olson |
| 6,897,780 B2 | 5/2005 | Ulrich |
| 6,917,293 B2 | 7/2005 | Beggs |
| 6,987,232 B2 | 1/2006 | Smith |
| 2004/0111045 A1 | 6/2004 | Sullivan et al. |

* cited by examiner

| BE Sensitivity Setting | IB Debounce Time (seconds) | Exiting Debounce Time (seconds) |
|---|---|---|
| BE alarm off | 10 | 10 |
| High | 3 | 1 |
| Medium | 6 | 3 |
| Low | 6 | 4 |

FIG. 9

| # | Rule | BE State | Notes & Examples |
|---|---|---|---|
| 1 | Section a-only is on for any zone combination | EXITING | 1: a(only, or with any sections in zone 3)<br>21: a(only, or with any sections in zone 3)<br>22: a(only, or with any sections in zone 3)<br>23: a(only, or with any sections in zone 3)<br><br>Any combination of 1a, 21a, 22a, 23a(with or without any sections in zone 3) |
| 2 | If sensors 1, 21, 22 & 23 are off(all sections) and sensor zone 3 is on (any section or section combination) | EXITING | 3: a, ab, abc, abcd, bc, abc, (ac) |
| 3 | If sensors are closed only in sensor zone 23. (with or without any sections in zone 3) | OOB | 23: a, b, c, d (any combination of these alone, or with any combination of sections in zone 3) |
| 4 | If any 2 or more sections are activated within zone 1. (Because zone 1 only contains 3 sections-1a&b are shorted, and there is some distance between zone 1 and the adjacent zone 21) | IB | 1: bc, cd, bd<br>(any combination of these, with or without any other sections activated) |
| 5 | If any 4 or more sections are activated within zones 1, 21, 22, or 23. Ignore exiting sensors(zone 3) | IB | 21: abcd  22: abcd<br>1bc & 21bc, 21ab & 22bc, 1cd & 23bd, 1 bc & 21bc & 22 bc,... |
| 6 | All sensors are off. | OOB | |

FIG. 10

| # | Rule | BE State | Notes & Examples |
|---|------|----------|------------------|
| 1 | A combination of sections a and b only are on for any zone combination | EXITING | 1: a,b(only, or with any sections in zone 3)<br>21: a,b(only, or with any sections in zone 3)<br>22: a,b(only, or with any sections in zone 3)<br><br>Any combination of 1ab, 21ab, 22ab, 23ab(with or without any sections in zone 3 and 23) |
| 2 | If sensors 1, 21, 22 are off(all sections) and sensor zones 23 or 3 are on (any section or section combination) | EXITING | 23: a, ab, abc, abcd, bc, abc, (ac)<br>3: a, ab, abc, abcd, bc, abc, (ac)<br>Any combination of the above sections. |
| 3 | If any 2 or more sections are activated within zone 1. (Because zone 1 only contains 3 sections-1a&b are shorted, and there is some distance between zone 1 and the adjacent zone 21) | IB | 1: bc, cd, bd<br>(any combination of these, with or without any other sections activated) |
| 4 | If any 4 or more sections are activated within zones 1, 21, 22, or 23. Ignore exiting sensors(zone 3) | IB | 21: abcd    22: abcd<br>1bc & 21bc, 21ab & 22bc, 1cd & 23bd, 1 bc & 21bc & 22 bc,... |
| 5 | All sensors are off. | OOB | |

FIG. 11

| # | Rule | BE State | Notes & Examples |
|---|---|---|---|
| 1 | If all sections in zone 1 are open. | EXITING | 21: abcd<br>22: abcd<br>23: abcd<br>Any combination of 21,22 and 23 a,b,c,d with any combination of sections in zone 3. |
| 2 | A combination of sections a and b only are on for any zone combination | EXITING | 1: a,b(only, or with any sections in zone 3)<br>21: a,b(only, or with any sections in zone 3)<br>22: a,b(only, or with any sections in zone 3)<br>Any combination of 1ab, 21ab, 22ab, (with or without any sections in zone 3 and 23) |
| 3 | If sensors 1, 21, 22 & 23 are off(all sections) and sensor zones 23 or 3 are on (any section or section combination) | EXITING | 23: a, ab, abc, abcd, bc, abc, (ac)<br>3: a, ab, abc, abcd, bc, abc, (ac)<br>Any combination of the above sections. |
| 4 | If any 2 or more sections are activated within zone 1. (Because zone 1 only contains 3 sections-1a&b are shorted, and there is some distance between zone 1 and the adjacent zone 21) | IB | 1: bc, cd, bd<br>(any combination of these, with or without any other sections activated) |
| 5 | If any 4 or more sections are activated within zones 1, 21, 22, or 23. Ignore exiting sensors(zone 3) | IB | 21: abcd   22: abcd<br>1bc & 21bc, 21ab & 22bc, 1cd & 23bd, 1 bc & 21bc & 22 bc,.... |
| 6 | All sensors are off. | OOB | |

BED EXIT AND PATIENT DETECTION SYSTEM

BACKGROUND OF THE INVENTION

The present invention relates generally to medical monitoring systems, and more particularly has reference to a new and improved system and method for providing an accurate and reliable indication of whether a patient in a hospital, nursing home, assisted living facility or other healthcare facility, is in bed, out of bed, or is actively attempting to exit the bed.

Monitoring patients is an important aspect of patient care in many different settings. In a general medical or surgical ward or floor of a hospital, for example, monitoring vital signs such as heart rate and respiratory rate is a basic component of patient care. Monitoring the presence or absence of a patient in his or her bed also may be beneficial in a general medical or surgical ward or other area of a hospital or healthcare facility. If certain patients leave their beds, they run a risk of falling and injuring themselves, or of becoming detached from important treatment apparatus such as IV lines, drainage tubes and like. Confused patients (e.g., those suffering from some form of mental disability), might become lost or wander off from the healthcare facility.

Current systems for patient monitoring used in most hospitals generally do not provide for constant, around-the-clock monitoring. Instead, on a general medical or surgical ward of a hospital, for example, monitoring typically consists of a team of nurses circulating from patient to patient, at three- or four-hour intervals, to take vital signs. In some hospitals, this monitoring may be augmented by one or more devices, such as a bedside pulse-oximeter, which monitors pulse and oxygen saturation via a small clamp-like device attached to a patient's finger. The method for determining whether a patient on bed restrictions actually remains in bed, often involves direct observation by a nurse or other caregiver.

Recently, some efforts have been made to develop a system for accurately measuring basic physiological parameters, such as heart rate and respiratory rate continuously, without the use of electrodes, leads or other devices that require direct attachment to the patient's body. The system is designed to utilize a signal processor with data collection sensors disposed invisibly in the patient's bed that produce an electrical signal in response to physiological patient stimuli as the patient lies in bed on the sensor device. Upon detecting a change signifying a deterioration in the patient's condition, the system is designed to notify and report the event to the care staff utilizing the hospital's existing nurse call system.

Bed exit systems of various kinds are known. Historically, physical restraints (such as vests, ankle or wrist restraints) were used to try to keep patients safe in healthcare facilities. In recent years, however, the healthcare community has come to recognize that physically restraining a patient can be dangerous. Bed rails are sometimes used as restraints, but these too have proven to be a safety concern. Additionally, some hospitals incur considerable expense to employ bed-sitters to watch patients, primarily to guard against unauthorized exiting the bed.

More recently, alarm-based systems of two types have been developed. There are bed-based systems designed to be attached to a bed or selectively deployed near a patient's bed as needed. There also are patient-applied systems, such as clips or RF sensors (bracelets) designed to be worn by the patient.

The bed-based alarm systems generally include integrated position sensor systems that are designed to be built into the bed structure in a permanent fashion. These systems are intended to be dedicated devices that generally rely on the use of advanced technology, such as load cells, capacitive sensors or resistive sensors, to sense a patient's weight and position on the bed. They tend to be costly and difficult to install and cannot be separated from the bed once they have been installed.

Pressure sensitive pad systems, on the other hand, are generally stand-alone devices intended to be selectively deployed, which require the use of obtrusive and cumbersome pads designed to be placed over a mattress, under the mattress, or on the floor near the patient's bed. Typically, these pad-type sensors are relatively small in size and provide only localized detection (e.g., one or two detection zones in the hip and occasionally shoulder areas). Typically, they are not designed for use with smaller or lighter patients or with in-bed vital signs monitoring systems.

Many of the existing pressure sensitive pad systems also are prone to false positives, i.e., the patient is in bed, but is sensed as being out of bed, resulting in unnecessary nuisance alarms that care staff must respond to. This deficiency often is due to the use of latching alarms, insufficient sensor size, insufficient sensitivity, impacts of the mattress and/or bedding, and the lack of a delay before actuating the alarm. Pad placement also tends to be critical with many of these designs, and many false alarms are caused by improper pad placement. Another drawback is the frequent occurrence of false negatives, i.e., the patient is out of bed, but is sensed as being in bed. This is a potential safety concern for a hospital patient on bed exit restrictions, as the patient may have fallen or be at risk for falling while no alert to care staff has been generated.

A need exists for an improved bed exit detection system that is more reliable than current pad systems and easier to use, but is more adaptable and less costly and complex than current integrated systems. Ideally, such a system would be capable of being retrofit to an existing hospital bed in a way that would be virtually invisible to the patient and staff. In order to enhance the work flow of nurses and other caregivers in a hospital or other healthcare facility, the system should alert reliably and accurately, and should be able to accurately detect virtually all in-bed conditions regardless of patient size, position or location in the bed (i.e., not be prone to false negatives). The system should be capable of alerting hospital staff not only when patients are out of bed when they have orders to stay in bed, but for some patients (such as slow moving patients, for example), of providing a warning before the patient actually exits the bed.

However, the general medical or surgical floor area of a hospital is a particularly challenging environment for a bed exit detection system. A system designed for use in such an environment needs to accommodate different kinds of beds, including flat beds and articulated beds (i.e., beds with articulated frame sections which can be angled upwardly in order to position the upper torso and head of the patient or the patient's feet, in a more upright fashion), and beds with full-length rails or half-length rails (i.e., rails that extend only along the upper torso portions of the bed), each of which presents possibly different bed exit scenarios. Most hospital beds in use today include some form of articulation and some form of a half-rail configuration, either a single half-rail in the torso area or split rails, i.e., two half-rails side-by-side, one in the torso area and another in the leg area, with a gap in between.

There are further factors as well which make the hospital a challenging environment for bed exit detection. Compatibility is necessary with a large variety of hospital beds and mattresses of differing size, weight and structure (e.g., a powered, fluid-filled mattress has different characteristics than a passive foam mattress). Hospital patients also come in a wide variety of sizes and weights, and while the majority of patients are supine with elevated head of bed, they may assume a variety of different positions on the bed, including side, prone or sitting positions, with the bed flat, or with the head or feet elevated. Additionally, hospital patients often sit up and eat in bed. Visitors in the patient's room provide another source of potential complications, since they might touch, lean on, or sit on the patient's bed, providing false indications. Hospital staff also tend to move or adjust the patient in the course of treatment. The presence of various kinds of bedding (such as pillows or support cushions), hospital equipment or other apparatus in the vicinity of a patient's bed also creates the risk of a foreign object on the bed that may potentially provide a false indication that a patient is present in the bed. Additionally, since hospital patients are in bed a high percentage of the time, wear and tear issues also can be a significant challenge.

Further challenges include the need for both remote and local alarms to alert the patient and care staff of possible bed exit conditions, and the need for a system which is comfortable to the patient and does not create a pressure distribution on the bed which could compromise skin integrity or the patient's health. Further, the system must be reliable, because there often is a minimal tolerance of false alarm by care staff, and should be flexible enough to accommodate the differing needs of different patients.

A bed exit system intended for use in the general medical or surgical floor area of a hospital or other institution also should be compatible with a remote in-bed vital signs monitoring system. Proper selection and relative placement of the different kinds of sensors used for vital signs and bed exit detection, respectively, thus becomes an important consideration. Ideally, means should be provided to maintain the integrity of those sensor placements, while allowing for easy adaptability to a variety of beds and bed configurations.

Thus, a need exists for a bed exit detection system suitable for use in the general medical or surgical floor areas of a hospital or other healthcare facility, which is compatible with a remote vital signs monitoring system, can be easily adapted to a variety of different kinds of beds, and which is sufficiently reliable both for in-bed and out-of-bed detection over the full range of patient positions and bed exit maneuvers commonly encountered in a hospital environment, so as to improve patient safety and care, free-up nursing staff for other important tasks, and improve overall clinical operations in the institution, all at a reasonable cost.

The present invention fulfills these and other needs.

SUMMARY OF THE INVENTION

Briefly, and in general terms, the present invention provides a new and improved patient monitoring system embodying novel methods and apparatus for more accurately and reliably detecting and evaluating a patient's position and sequence of positions on a bed to determine whether a patient is in bed, is out of bed, or is likely to be exiting the bed. The system is easy to use, can be retrofit to existing beds, and is particularly well suited for integration with a vital signs monitor in the general medical or surgical floor area of a hospital, nursing, home, or other healthcare facility.

In accordance with the present invention, reliable in-bed detection is provided by a plurality of pressure sensors located in the torso and hip areas of the patient's bed to detect when a patient is in the bed. By using multiple sensors at discrete locations along the length and width of the bed, and redundant detection of sensor signals to confirm an in-bed condition, the patient is able to move around normally in bed and assume a variety of different positions in the bed without activating an alarm, and there is a minimum risk of a false in-bed determination. By advantageously integrating this reliable in-bed determination capability with an associated vital signs monitoring system, the overall accuracy and reliability of the vital signs monitoring system can be improved as well. For example, the reliable in-bed detection can be used to avoid errors in vital signs monitoring, whether or not the bed exit alarm is enabled or disabled.

Separately, the system also provides for reliable bed exit detection to determine if a patient is out of bed or has assumed a position or sequence of positions near the foot or sides of the bed, indicating a likelihood that the patient is in the process of exiting the bed. In at least one aspect of the invention, the separate bed exit detection is provided by a plurality of sensors in the leg area of the bed to detect a patient moving toward an egress point near the foot of the bed, and/or by plurality of sensors at the sides of the bed to detect a patient moving toward an egress point at the sides of the bed or sitting on the edge of the bed. The system alarms promptly (within a few seconds) when a patient is completely out of bed, and in many cases, will alarm before the patient fully exits the bed. The bed exit alarm is user selectable (on/off), so that it can be turned off by the caregiver for patients who are not on bed restrictions.

By providing a separate bed exit detection scheme, the occurrence of false positives is reduced, especially in the case of restless patients who tend to move around a lot in bed. The separate exit detection insures that the bed exit alarm will not sound unless such a patient is truly getting out of bed by moving along a typical exit path on the bed surface.

The system allows the clinician to select the desired sensitivity level for each patient, allowing some patients more freedom of movement than others, before an alarm indication is provided. In some cases, the system can be set to alarm not only when the patient is exiting the bed, but also when the patient tries to assume certain clinically significant positions in bed which the clinician deems undesirable for that particular patient for health reasons or because the patient is undergoing certain forms of treatment. Examples of such non-exit conditions for activating a bed exit alarm include sitting positions and slumping positions in bed.

In addition, by advantageously integrating the bed exit detection system with a vital signs monitoring system, the bed exit sensors can be arranged to detect when a patient is in bed, but is not properly placed in the vital signs monitoring area of the bed (e.g., is not in proper communication with the vital signs sensors disposed in the patient's bed). A suitable warning or other corrective action can be taken when such a condition is found to exist.

The system is useable with different kinds and sizes of beds and with a wide range of patient populations. It can be used with small patients (e.g., approximately 100 pounds) or larger patients.

The system is not prone to false alarms, nor is it prone to false negatives. It detects patient elopement or imminent elopement (depending on the sensitivity setting) and alarms promptly (if activated). The sensor system is essentially invisible to the patient and hospital staff, is soft, comfortable and durable, and is easily adaptable to different hospital beds.

As previously noted, the system accommodates a wide variety of patient positions on the bed, including supine (lying on back), prone (lying on stomach), sitting positions, and patients lying on their side. As such, it reliably detects when a patient is lying in bed in all of the common in-bed positions encountered in a hospital or nursing home environment, including elevated head of bed, elevated foot of bed, or combinations of elevated head and foot. The system allows for normal patient movement up and down the bed toward the head or foot end of the bed, as well as movement left and right on the bed surface. Accommodation has been made for both static movement (i.e., different body positions on the bed) and dynamic movement (i.e., active patient motion).

The system also accounts for the fact that a variety of a different bed exit scenarios are possible when a patient tries to exit a hospital bed. Typically, at least some rails are up for a patient on bed exit restrictions. Thus, for example, on a flat bed with full-length rails, the patient may scoot to the end of the bed and try to exit over the footboard. In contrast, in a flat bed with half-length rails, the patient may try to sit up, scoot down past the end of the rail and exit slowly in the gap between the rail and the footboard. In beds with elevated back and foot sections and split side rails, the patient may try to squeeze through the gap between the rails midway along the length of the bed.

Generally, the system will provide an in-bed, out-of-bed, or exiting bed indication only when the sensors detect such a condition continuously for a pre-determined minimum period of time (known as debounce time). This reduces the risk of false alarms and false negatives. Different debounce times can be used for different situations. Thus, for example, in one embodiment, the system will alarm promptly (within a few seconds) when the patient is attempting to exit at the foot of the bed or is sitting at the foot portion of the bed. The system also will alarm within a few seconds when the patient is poised in an imminent elopement position at the extreme side edge of the bed (e.g., a position immediately prior to shifting weight to his feet, but after his legs are off the side of the bed), or is otherwise moving too close to the sides of the bed. These are the most common bed exit modes encountered. In contrast, the system will alarm more slowly (e.g., within ten seconds) in unusual or unexpected exit cases (such as, for example, when the bed rails are down and a patient exits quickly at the sides of the bed). The additional time delay insures that notice is provided only when the patient is actually gone (eloped) from the bed, and thus helps to avoid false positives.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 9 is a table showing a set of low sensitivity bed exit logic rules, in priority order, from top (highest priority) to bottom (lowest priority);

FIG. 10 is a table showing a set of medium sensitivity bed exit logic rules, in priority order, from top (highest priority) to bottom (lowest priority);

FIG. 11 is a table showing a set of high sensitivity bed exit logic rules, in priority order, from top (highest priority) to bottom (lowest priority)

DETAILED DESCRIPTION OF THE PREFERRED EMBODIMENTS

Figure 1:
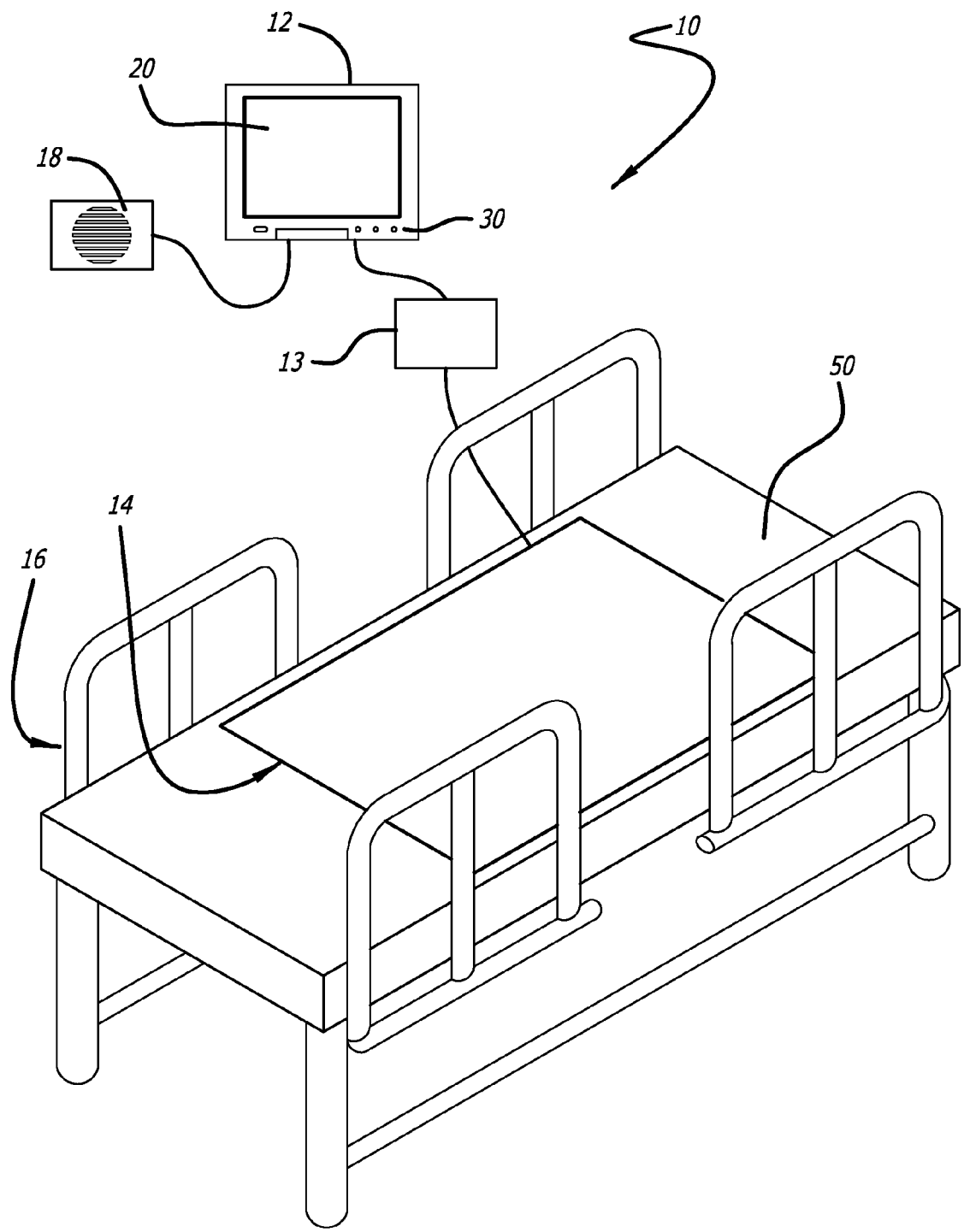
FIG. 1 is a schematic view of a patient monitoring system embodying the novel features of the present invention and showing the system connected to a bed and to a standard nurse call system in a hospital, nursing home or other institution.

As shown in the drawings for purposes of illustration, the invention is embodied in a patient monitoring system 10 having a bedside unit 12 connected to a sensing array 14 placed under the patient in a typical hospital bed 16 and to an existing hospital nurse call system 18 via an interface within the bedside unit. The bedside unit 12 houses a signal processor and an alarm processor to analyze the data received from the sensing array 14 and to activate an alarm when a clinically significant event is occurring. A pre-processor and signal conditioning circuit 13 also is provided to interface the sensing array 14 with the processor in the bedside unit 12.

The bedside unit 12 is typically a wall-mounted unit with a display 20 that becomes activated (turns on) only when an alarm condition is detected or on command by the nurse, by touching a key on the unit 12. Alternatively, the display can be configured to remain on at all times. The bedside unit 12 may be provided with a number of dedicated and soft key buttons and other user controls 30 for entering information, setting up specific items and interfacing with the system. A memory within the bedside unit 12 stores software programs and other information to be used by the processor in analyzing the signals received from the sensing array 14.

Figure 4:
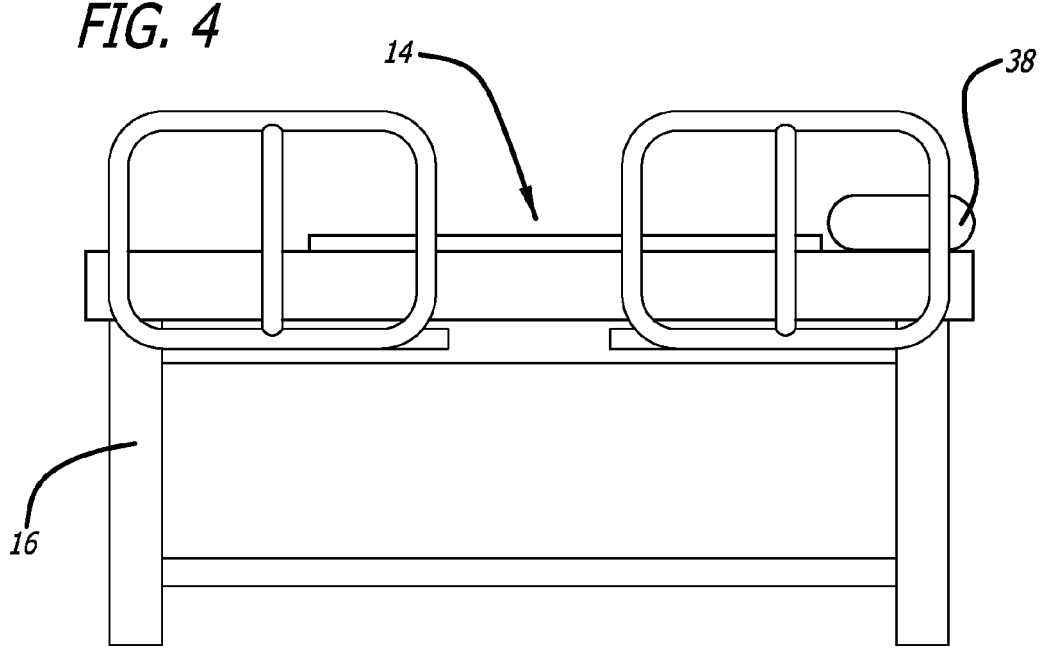
FIG. 4 is a side elevational view of the bed shown in FIG. 1 in a flat bed position.
Figure 5:
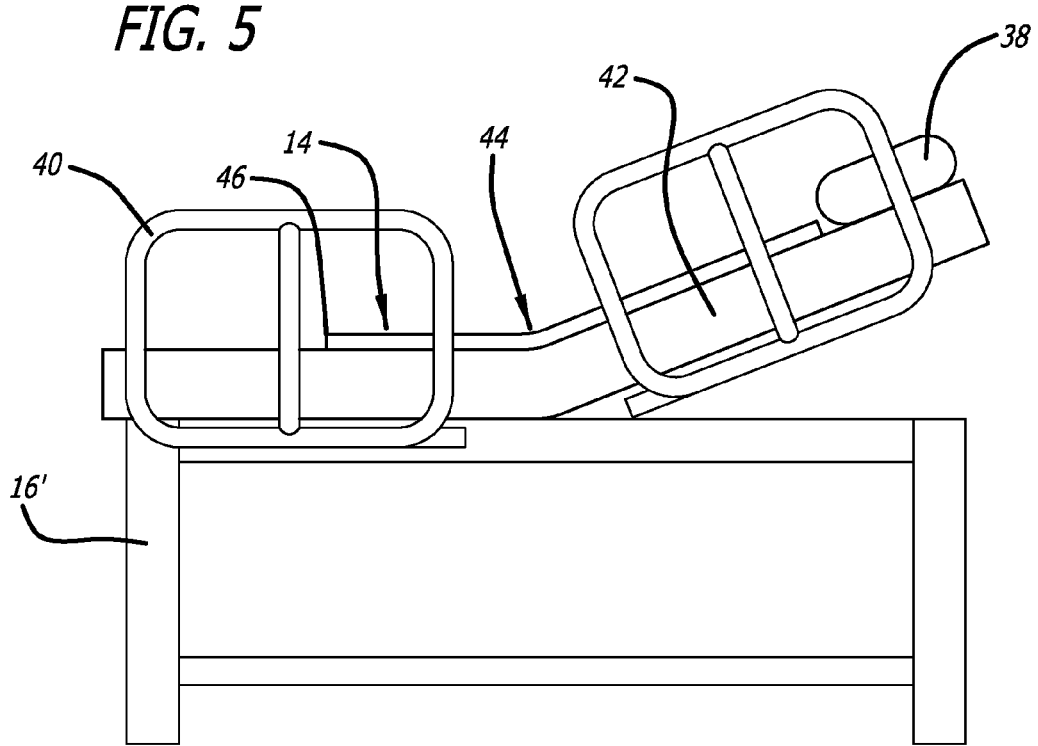
FIG. 5 is a side elevational view of the bed shown in FIG. 1 in a back elevated position.

While various types of sensor devices can be used, in one embodiment, the sensing array 14 includes a plurality of thin piezoelectric sensing films or other similar sensing technology for sensing a patient's vital signs or other physiological parameters, and a plurality of pressure sensors disposed between the piezoelectric films which produce a pattern of signals indicative of whether a patient is in bed, out of bed, or is actively in the process of exiting the bed. In one embodiment, more than thirty individual pressure sensors are used to cover the area from the patient's shoulders to upper legs. Both the piezoelectric films and pressure sensors are placed in the bed, under the bed sheets, without any direct attachment to the patient's body. The sensing array 14 in FIGS. 1, 4 and 5 is shown disposed on top of a mattress coverlet 50 for ease of illustration, but in most cases, it will be advantageous for the sensing array 14 to be attached to the inside of the top surface of the coverlet for invisibility in use, ease of retrofit to existing hospital beds, and to protect the sensing elements and circuits from moisture and provide for added patient safety.

The signal processor within the bedside unit 12 is made up of hardware and software that accepts, buffers and converts the signals from the piezoelectric sensors from analog to digital form for processing to determine a patient's vital signs or other physiological parameters. For a full description of the sensing capability of piezoelectric films, their use in sensing patient parameters and methods to process the signals from these films to generate cardiac, respiratory and other physiological signals, reference may be had to a co-pending patent application commonly assigned to the same assignee as the present invention, U.S. patent application Ser. No. 10/301,525, entitled "Devices and Methods for Passive Patient Monitoring," filed Nov. 20, 2002, the full disclosure of which is incorporated herein by reference. Methods for integrating piezoelectric films and pressure switches into a patient's mattress are described in another commonly owned, co-pending application, namely, U.S. patent application Ser. No. 11/061,213, filed Feb. 18, 2005, and entitled "Method and System for Integrating A Passive Sensor Array With A Mattress for Patient Monitoring," the full disclosure of which also is incorporated herein by reference.

The vital signs data, such as heart rate and respiration rate, and other physiological parameters derived by the signal processor, may be displayed in real time in numeral and/or graphical form on the display screen 20 of the bedside unit 12, or they may be recorded in memory for subsequent playback and review.

In addition to having a signal processor that derives physiological data, the bedside unit 12 also includes an alarm processor. The alarm processor uses logic to monitor the patient parameter trends and determine when a negative condition is occurring. It activates a physiological alarm to warn of potentially adverse conditions. An alarm circuit is provided in the bedside unit 12 for generating a local alarm in the patient's room and/or a remote alarm through the nurse call system 18 already installed in the hospital or healthcare facility. A suitable alarm system is described in a commonly owned, co-pending application, U.S. patent application Ser. No. 11/004,589, filed Dec. 3, 2004, and entitled "Intelligent Medical Vigilance System," the full disclosure of which is incorporated herein by reference.

In addition to monitoring the patient's physiological parameters, the software inside the bedside unit 12 also is programmed to continually observe the state of the various pressure sensors and use logic to determine, from the pattern of sensor states observed, whether the patient is in bed, out of bed, or is attempting to exit the bed. For patients who are restricted from exiting the bed, a nurse or other clinician can selectively activate a bed exit alarm. The bed exit alarm will sound when the system detects that a patient on bed exit restrictions has left the bed or is actively attempting to exit the bed but does not have permission to do so. In some embodiments, the alarm also will sound if a patient is determined by the processor to be attempting to sit up in bed without permission, or is slumping down toward the foot of the bed. The alarm can be selectively disabled by the caregiver for a patient who has permission to exit the bed, such as a patient with bathroom privileges, walking privileges, or the like.

Depending on the setting, the unit 12 may alarm locally in the patient's room and/or through the existing nurse call system 18. The local alarm can consist of a beep or a prerecorded voice announcement warning the patient to "get back into bed." The voice announcement can be custom recorded in the language of the patient. Generally, the bed exit alarm may be configured to be different from any physiological alarm raised by the vital signs portion of the monitoring system.

In one aspect of the invention, the bed exit alarms are non-latching, meaning that if a patient moves to a position on the bed in which the bed exit alarm is raised, but then returns to an in-bed position, the alarm will be automatically turned off without the need for caregiver intervention. Thus, for example, if an alarm sounds because a patient is getting out of bed without permission, but the patient responds to a "get back in bed" message and returns to the bed, the local alarm in the patient's room will be canceled. On the other hand, the signal to the nurse call system 18 may be latched or unlatched, as desired, depending on how the system is configured for the particular hospital or healthcare facility.

Figure 2:
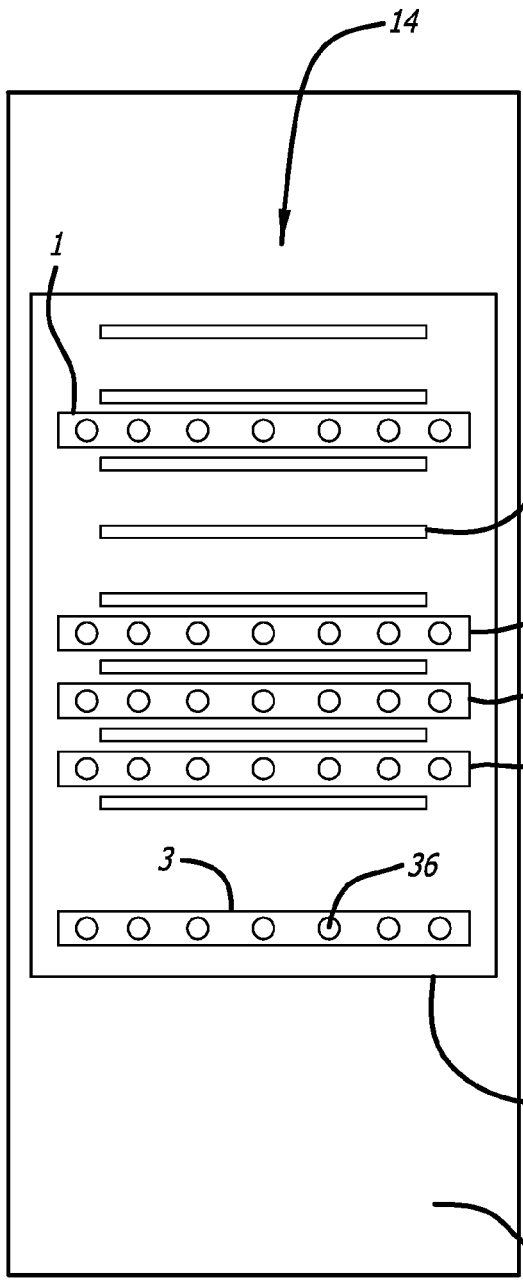
FIG. 2 is an enlarged plan view showing in schematic form one embodiment of a layout of vital signs sensors and bed exit sensors disposed on the bed in FIG. 1.
Figure 3:
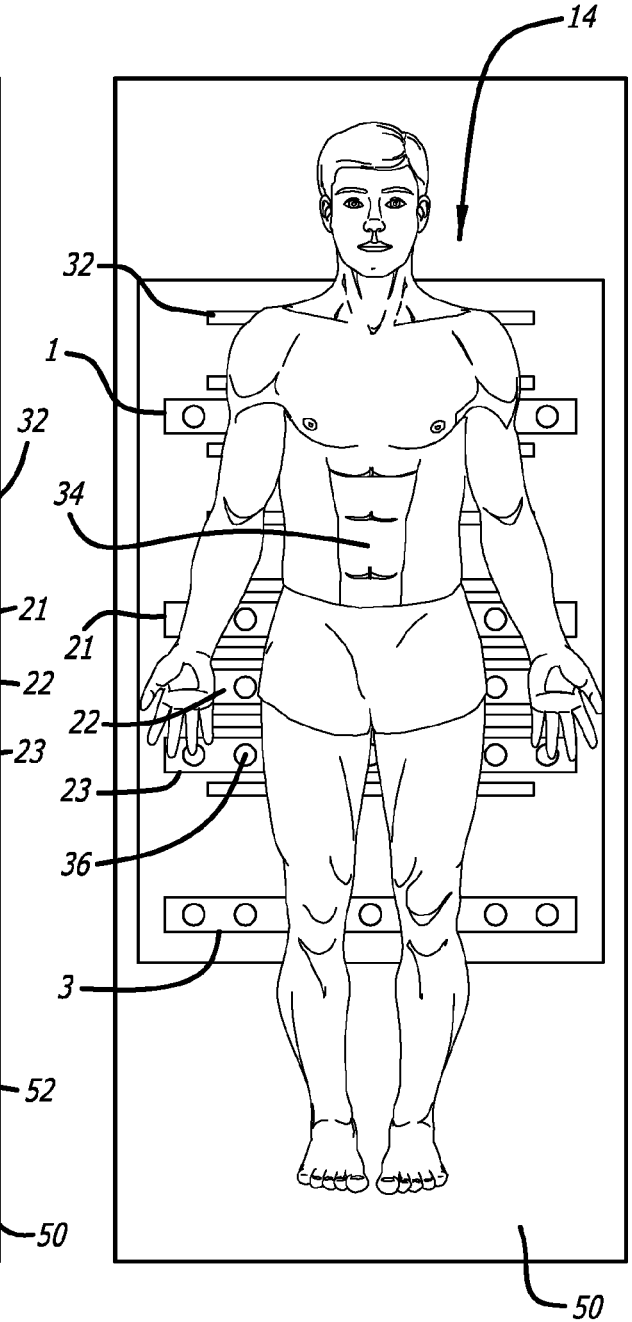
FIG. 3 is a plan view showing a patient positioned on the layout of sensors illustrated in FIG. 2.

Referring to FIGS. 2 and 3, there is shown a schematic diagram which is illustrative of one possible layout of piezoelectric film sensors and pressure sensors for use with the present invention.

The layout of FIGS. 2 and 3 includes a plurality of piezoelectric film strips 32 that run laterally across the bed 16 in a pattern that spans most of the patient's body 34 from the shoulders to the thighs. Although different configurations and numbers of film strips 32 can be used, in the illustrated embodiment, eight identical films of equal size and shape are arranged in a spaced-apart, parallel configuration. The piezoelectric strips 32 may be constructed of polyvinyledene fluoride (PVDF) film, or other polarized polymer film with piezoelectric properties, and the entire array of films affixed to the inside of the top surface of a mattress coverlet. Electrical signals are conducted from each film strip 32 by conductive traces and wires (not shown) through the signal conditioning circuit 13 to the bedside unit 12 for processing to derive the desired vital signs data.

As shown in FIGS. 2 and 3, the sensor array 14 also includes a plurality of pressure sensors 36 incorporated into the array between the piezoelectric strips 32 for determining in-bed or bed exit conditions. While various numbers of sensors 36 can be used, in the illustrated embodiment, a total of thirty-five sensors 36 are arranged in a pattern to cover the area of the mattress from a patient's torso to legs. In addition, it is desirable for the pressure sensor array to extend laterally beyond the ends of the piezoelectric strips 32, to insure adequate coverage of the vital signs monitoring area. Many different kinds of pressure sensors 36 can be used, but round, flat pressure switches, such as membrane switches, are especially suitable for use with the present invention. Those switches 36 can be mounted to the inside of the top surface of a coverlet along with the piezoelectric strips 32, and electrically connected to the bedside unit 12 in a manner to be described. Software inside the bedside unit 12 is programmed to continually observe the state of these switches to determine whether the patient is in bed, out of bed, or is actively attempting to exit the bed. If desired, sensors of different sensitivity can be used in different areas of the bed. For example, more sensitive sensors 36 can be used in parts of the torso area of the patient's bed.

Each switch 36 in the array 14 is identified by a unique zone and section designation. In the illustrated embodiment, as best shown in FIGS. 2 and 3, the switches 36 are arranged into five zones. Each zone is a rectangular strip of sensors 36 extending laterally across the bed 16. One zone (zone 1) is arranged to be located in the torso and, especially near the mid-back region of a typical adult-sized patient reclining on the bed. Three closely spaced zones (zones 21, 22 and 23) are arranged in the patient's hip area. Another zone (zone 3) is located in the mid-leg area. A gap of some distance is maintained between the head end of the mattress and the mid-back zone 1, the mid-back zone 1 and the hip zones 21, 22, 23, between the mid-leg zone 3 and the hip zones 21, 22, 23, and between the mid-leg zone 3 and the foot end of the mattress, respectively. Costs are reduced by leaving these gaps free of bed exit sensors, which would add little to the overall effectiveness of either the in-bed or existing bed detection schemes. The mid-leg sensor zone 3 is placed to detect patient movement toward the footboard or toward the gap in the side rails near the footboard, thus covering both possible exit maneuvers.

In the illustrated embodiment, all the zones 1, 21, 22, 23, 3 are arranged parallel to each other, and each zone contains seven individual switches 36 placed at discrete, equally spaced locations across the bed 16 within the zone. In at least one embodiment, the switches 36 are positioned so as to provide sufficient left-to-right coverage for a standard size mattress. The use of rectangular strips permits side-to-side patient movement, particularly for a patient 34 lying on his or her side. The use of multiple zones 1, 21, 22, 23, 3 in the areas described also allows for some degree of up/down patient movement on the bed surface. The gaps between switches (within a zone) provide cost savings by minimizing the size and number of switches employed while not being so large so as to reduce ability to detect patients, especially a small patient lying on his or her side. Additionally, all sensors (piezo and pressure) run parallel along the left-right axis of bed so as to minimize the amount of material at the articulation point of the bed and to minimize wrinkling and bending of sensors, extending product life as well as minimizing wrinkles which may create localized areas of increased pressure applied to the patient.

It will be appreciated that the number of zones can be increased or decreased from those shown in FIGS. 2 and 3. Thus, for example, an additional zone can be added above zone 1 for greater sensitivity and resolution in the upper torso area of the bed. It also may be possible, in at least some embodiments, to eliminate zone 3 in the leg area of the bed.

With reference to FIGS. 4 and 5, the sensor array 14 is shown schematically disposed on a hospital bed 16. As shown in FIG. 4, the sensor array 14 extends longitudinally along a flat bed surface from the region just below the patient's pillow 38 to the region of the bed 16 near the patient's knees. As shown in FIG. 5, the sensor array 14 is schematically disposed on an adjustable bed 16' with half-length, split-side rails 40 and an elevated back 42 having multiple height options. As shown in FIG. 5, the sensor array 14 covers the elevated back portion 42 of the bed 16' from just below the pillow region 38 to the articulation point 44, and from the articulation point 44 to the region of the bed 46 near the patient's knees and legs, generally corresponding to the area just below the gap between the rails and the footboard of the bed (or in a bed with two half-length rails on each side of the bed, the gap between the rails). The articulation point 44 is generally disposed in the area of the three zones 21, 22, 23 near the patient's hips, with at least the lowermost zone 23 disposed below the articulation point 44. In some beds, all three zones 21, 22 and 23, may be disposed below the articulation point 44, due to differences in the location of the articulation point 44. If desired, the sensor area can be assembled in two separate pieces, with zone 1 being contained in a torso piece and zones 21, 22, 23 and 3 being contained in a hip/thigh piece, for ease of construction, and to more readily accommodate the articulation point 44 without the necessity of bending of the sensor array or its supporting structure.

While the number of zones and the number of switches in each zone can be increased or decreased, the above-described arrangement balances cost, coverage and signal processing needs. An increase in the number of zones or the number of sensors in the zones will provide greater resolution and less opportunity for "dead spots" on the bed surface, but will increase costs and increase signal processing requirements (due to an increase in the number of signal processing channels). A decrease in the number of zones or the number of sensors in the zones may increase the risk that certain conditions may be inadvertently missed, especially in-bed conditions. Seven sensors per zone is believed adequate to detect all reasonable patient positions in bed without using extra numbers of sensors. A range of five to eight sensors per zone also may be suitable for many applications.

As previously noted, each zone is assigned a unique number (1, 21, 22, 23, 3). Zone 1 is the zone in the torso area. Zones 21, 22 and 23 are the three zones in the hip area. Zone 3 is the zone in the leg area.

Figure 6:
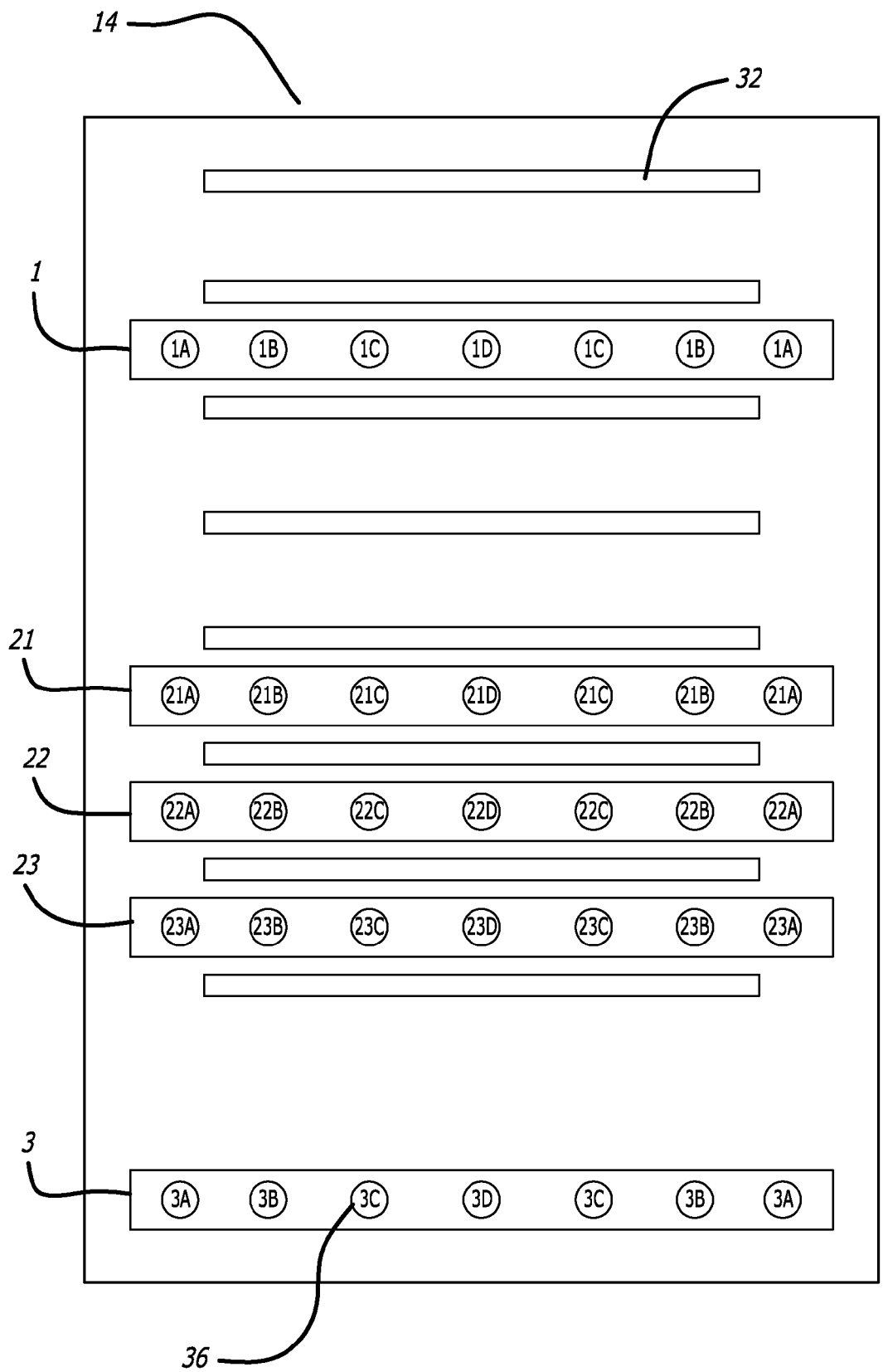
FIG. 6 is an enlarged plan view of the sensor layout of FIG. 2, showing the zone and section designations.

Each zone is further subdivided into seven sections, with each section containing one sensor or switch 36. Each section is assigned a letter designation. The sections are labeled a, b, c, d, c, b, a, respectively, as you move from left-to-right (or right-to-left) across the bed. The sensors 36 on the left and right sides of the bed 16 are wired in parallel for symmetry about the centerline of the bed, which is why each zone contains two sections a's, two section b's, and two section c's. The combined bed exit zone and section designations for the entire sensor array are illustrated schematically in FIG. 6.

Figure 7:
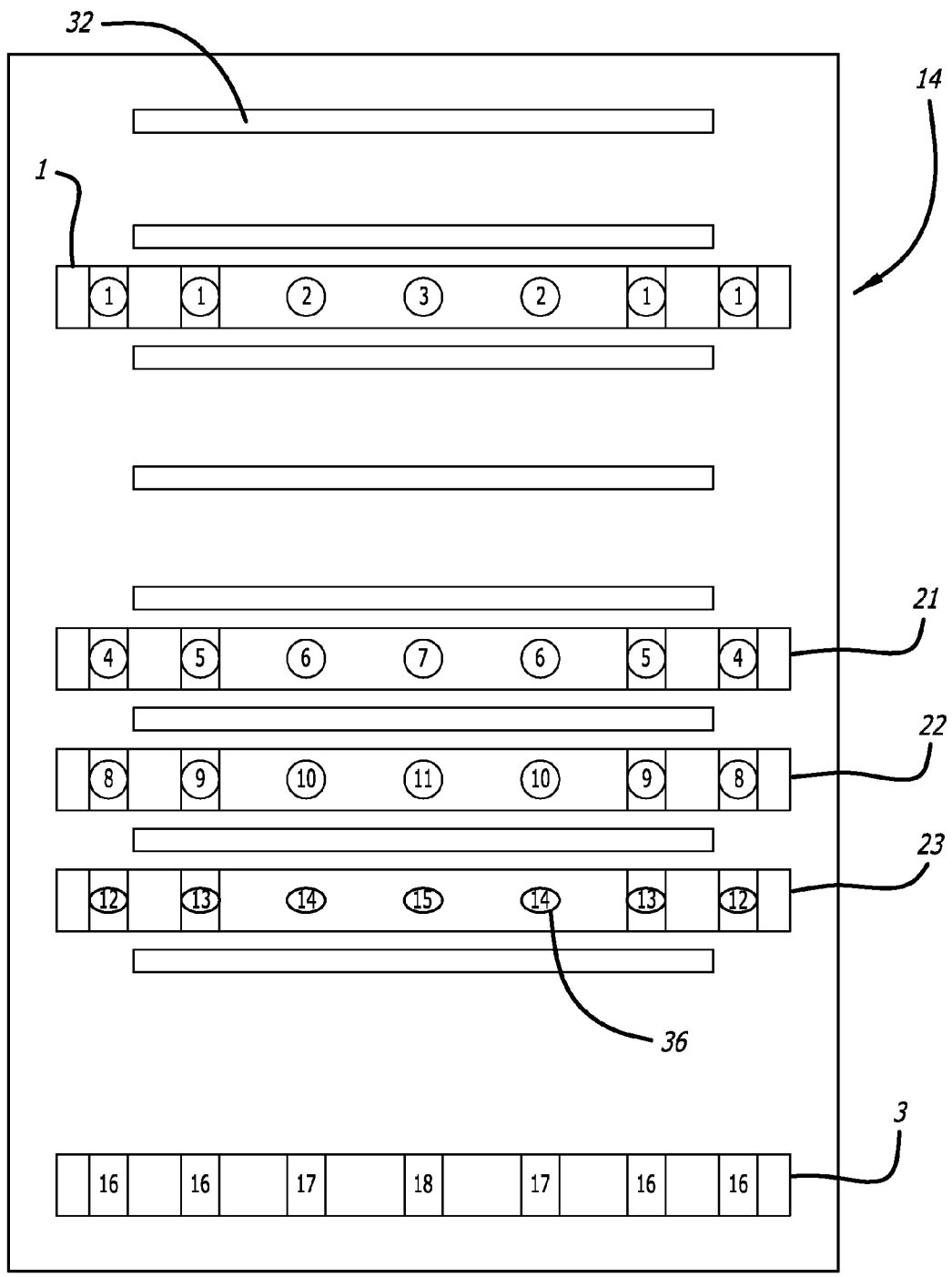
FIG. 7 is an enlarged plan view of the sensor layout of FIG. 2, showing schematically the sensor function and channel number assignments.

In general, each switch or sensor with a unique zone and section designation is assigned a unique bit number and is electrically connected to a separate input channel of the processing circuitry. On the other hand, each switch with a common zone and section designation is assigned the same bit number and is connected to the same input channel. Variations are possible, however, where it is desired to reduce the signal count or to provide variable signal resolution across a zone. Thus, for example, in the embodiment shown in FIG. 7, sections 1a and 1b are shorted and connected to the same input channel and assigned the same bit number. The same is true with respect to sections 3a and 3b. Other sections could be shorted as well, if desired. Combining sections in this manner results in data reduction and a reduction in the number of signal processing channels. Thus, for example, the arrangement shown in FIG. 7 permits the use of an eighteen channel signal processor for a thirty-five sensor array. Shorting adjacent sections also produces a variable signal resolution in zones 1 and 3, with a higher resolution in the middle of the bed being provided. Variable resolution alternatively can be achieved by the use of non-uniform sensor spacing across a zone. The bit assignments and channel numbers for the entire array are shown graphically in FIG. 7. The bit numbers enable the processor to keep track of which switches are open (off) and which switches are closed (on).

In one aspect of the invention, the bed exit switches 36 are arranged in such a way that at least some of the switches are used primarily to detect that a patient is in the bed. Generally speaking, in the illustrated embodiment, these are the switches in the central portions of zones 1, 21 and 22 located in the torso and hip areas of the bed 16. These switches 36 are identified as in-bed ("IB") sensors in FIG. 7. On the other hand, other switches 36 are used primarily to detect that a patient is in the process of exiting the bed 16. Generally speaking, these switches 36 are the ones near the foot of the bed 16 and are identified as "Exiting Sensors" in FIG. 7. Some of the switches, namely, those at the ends of zones 1, 21, 22 and 23 are dual function sensors used to detect both in-bed and exiting bed conditions. They are labeled as such in FIG. 7. The switches in zone 23 have a hybrid function (which will be described later). In at least one embodiment, these switches 36 function as in-bed (IB) sensors, but only in combination with one or more switches in zones 1, 21 and 22.

As previously noted, the signal processor within the bedside unit 12 is programmed to monitor the state of the bed exit switches 36 and to translate the switch states into a clinically relevant indication as to whether the patient is in bed, out of bed, or actively attempting to exit the bed. For software purposes, the out-of-bed ("OOB") and exiting bed ("EXITING") conditions are treated synonymously, in that both are alarm conditions for a patient on bed exit restrictions.

The primary functional difference between the OOB and EXITING indications is in how quickly the alarm activates, determined by which debounce time is used. All bed exit data is debounced by extending each switch closure in time in order to prevent false alarms and allow for motion tolerance. The amount of time each switch closure is extended is called debounce time. The debounce time is dependent upon the bed exit sensitivity setting (a user selection) and the bed exit logic rules used.

Figures 8, 12:
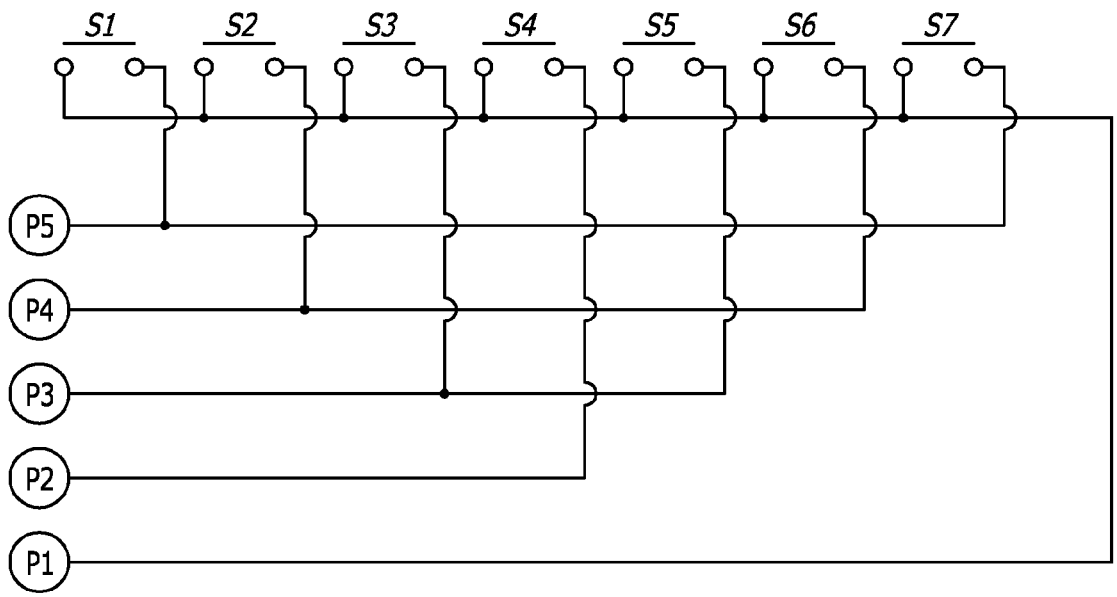
FIG. 8 is a table showing typical debounce times for various sensitivity settings.
FIG. 12 is a schematic diagram of a switch circuit suitable for use in one of the zones of the present invention.

As shown in FIG. 8, typical debounce times suitable for use with the present invention range from one to ten seconds, with the shorter "Exiting Debounce Time" being used to allow a quicker response when the patient is exiting the bed 16. The longer "IB Debounce Time" is used for in-bed detection and also is used when the switches 36 sense that a patient is attempting to exit the bed 16 in a manner other than as described in the logic rules, such as when a patient is detected transitioning directly from an IB state to an OOB state. The use of the longer debounce times under those circumstances helps to prevent false alarms due to unusual patient movement. The longest debounce times typically are used when the bed exit alarm is switched off, and the bed exit sensors 36 are being used solely to arm/disarm the physiologic alarm, as will be described. Debounce times other than those shown in FIG. 8 also can be used, in some embodiments.

As shown in FIG. 8, different debounce times can be used to provide varying levels of sensitivity and speed of response. The "Exiting Debounce Time" values shown in FIG. 8 were selected on the basis of experimental data, and are typical of times between when an exit sensor is activated and when the corresponding out-of-bed condition occurs. Likewise, the "IB Debounce Time" values shown in FIG. 8 were selected on the basis of experimental data, and are typical of the times between an initial IB sensor activation and the ability to reliably confirm an in-bed condition.

Many factors affect the overall sensitivity of a bed exit detection system, i.e., its ability to reliably detect both in-bed and bed exit conditions. In general, it is desirable to capture a person getting out of bed as early as possible. However, a number of trade-offs are often involved. The present invention was designed to minimize out-of-bed false positives, i.e., a patient in bed, but sensed as being out of bed, which is both a safety issue and a nuisance issue. It also was designed to minimize exiting false negatives, i.e., a patient exiting the bed, but not sensed. This is another safety issue, especially for patients at risk for a fall and because staff is unaware that a patient has left the bed. In addition, the system was designed to minimize out of bed false negatives, i.e., the patient is out of bed, but sensed as being in bed (another nuisance issue) and to minimize exiting false positives, i.e., a patient is in bed, but is sensed as exiting the bed (yet another nuisance issue).

The processor may include any number of bed exit sensitivity settings. In some embodiments, a single setting can be predetermined by the manufacturer or the healthcare facility. In other embodiments, different sensitivities can be selected by the caregiver depending on the individual patient needs. In the illustrated embodiment, three different sets of bed exit logic rules and debounce times are stored in the processor memory to allow the clinician, nurse or other caregiver to chose between low/medium/high sensitivities, or bed exit privileges (i.e., alarm off), for any particular patient.

FIG. 9 is a table showing a typical set of low sensitivity bed exit logic rules, in priority order from top (highest priority) to bottom (lowest priority). The rules assume a debounced data set, and are prioritized, such that if you proceed down the list and find a rule that applies, none of the rules below it on the list are applicable at that point in time.

From the table, it will be appreciated how the sensor array and logic rules provide both an in-bed detection function and a separate bed exit detection function. Thus, the in-bed detection function is provided primarily by the sensors in zones 1, 21, 22 and 23, near the patient's back and hips. In accordance with logic rule Nos. 4 and 5, an in-bed (IB) signal is provided if any two or more sensors 36 are activated in zone 1 for the applicable debounce time (indicating that the patient's back is lying on the bed in a common position), or if any four or more sensors 36 are activated in any combination of zones 1, 21, 22, and 23 for the applicable debounce time (indicating that the patient's hips or a combination of his hips and back are lying on the bed 16 in a common position). By relying on redundant detection (i.e., multiple sensor activations) to provide an in-bed indication, the patient is able to assume different positions in bed (static) and to move dynamically in bed without tripping the bed exit alarm. The use of redundant detection also minimizes the occurrence of false in-bed indications which could be caused, for example, by a visitor leaning on the bed with his or her hands, by a foreign object (e.g., a suitcase or a piece of equipment) on the bed, or by a patient assuming an unusual position in bed, such as kneeling or standing on the bed. The differential weighting given to the back and hip area sensors in the logic rules (i.e., the difference in the number of switch closures needed for an IB indication) is a reflection of the fact that the position of the patient's back on the bed is generally a more reliable indicator of an in-bed condition than merely his hip position. It also is due to the fact that there are fewer sensors to detect the patient's back, in this particular embodiment.

The particular arrangement of sensors 36 at multiple discrete locations within the multiple in-bed detection zones 1, 21, 22, 23 also allows for a certain amount of side-to-side and up/down patient movement on the bed 16 without tripping an alarm or missing a true IB condition. This feature can be especially useful with a restless patient who tends to move around in bed.

Under these low sensitivity logic rules, the separate exiting detection function is provided primarily by the sensors 36 near the sides of the bed (section a) and those near the foot of the bed (zone 3). The activation of any switch in section a alone for any combination of zones 1, 21, 22 or 23 or of any switch in zone 3 alone for the applicable debounce time provides an indication that the patient has moved to a typical exit position near the sides or the foot of the bed and thus may be attempting to exit the bed without permission. (Logic rule Nos. 1 and 2.) The ability to detect these various different bed exit modes is an advantage in a hospital setting or other environment, especially where hospital beds are used in place of regular style beds found in a typical home. By providing a separate exit detection region, the patient is able to move around in the central portion of the bed while minimizing the occurrence of false positive alarms.

It should be noted that the switches in zone 3 are not used alone. Instead, they are used in combination with the switches in zones 1, 21, 22 and 23. Thus, in the illustrated embodiment, an EXITING signal will not be provided unless the sensors 36 in zone 3 are "on" (closed) and all the sensors 36 in zones 1, 21, 22 and 23 are "off" (open). In this way, the system rules out a patient who is lying in bed and moving his legs or feet so as to activate the sensors 36 in zone 3, thus avoiding false positives for a patient who is actually lying in bed and not attempting to exit the bed.

The sensors in section "a" effectively overlie the end portions of zones 1, 21, 22, 23 and 3, and act as tripwires to catch a patient exiting at any side location up/down the length of the mattress. Thus, activation of any one or more of the switches 36 in section "a" only for any of zones 1, 21, 22 or 23 (with or without any sections of zone 3), will produce an EXITING signal, indicating that the patient is at the edge of the bed.

The aforementioned bed exit logic rules are specifically designed to provide an EXITING indication for the most common bed exit maneuvers encountered in a typical hospital setting, namely, slow movement towards the foot or sides of the bed. For less common exit maneuvers (e.g., rapid exit at the sides of the bed with the bed rails down, quickly scooting down and sitting at the foot of the bed with the bed rails up, or vaulting over the bed rails), the logic rules will detect a direct transition from an IB to an OOB state, sounding the bed exit alarm (if set) after the longer IB debounce time. The longer IB debounce time is used to minimize the occurrence of false positives when these particular scenarios occur.

In the particular embodiment shown in FIG. 9, zone 23 (which typically resides low in the patient's hip area) is used to detect a patient who is sitting up in bed but who may have slumped down toward the foot of the bed for some reason and may need assistance. This position has been associated with signs that an adverse condition may be occurring. For that reason, the activation of any switch in zone 23 alone (with or without with any switch in zone 3) for the applicable debounce time will produce an OOB signal to summon the nurse or healthcare provider to check on the patient's condition.

The low sensitivity setting uses the longest debounce times, as previously noted, in order to give priority to the suppression of false alarms.

FIG. 10 is a table showing a typical set of medium sensitivity bed exit logic rules, in priority order from top to bottom. These medium sensitivity rules also assume a debounced data set.

It will be appreciated that the medium sensitivity logic rules are similar to the low sensitivity logic rules, except that the regions near the sides and foot of the bed where an EXITING condition will be indicated, have been expanded in size. Thus, an activation of sensors 36 in sections a and b only for any zone combination will produce an EXITING signal, indicating that the patient has moved towards the side of the bed. Likewise, an activation of one or more switches in zones 23 or 3 only, will produce an EXITING signal, indicating that the patient may be trying to exit near the foot of the bed. In both cases, the bed exit alarm will sound sooner than it would have sounded with the lower sensitivity setting shown in FIG. 9. Also, it will be recalled that the debounce times are generally shorter with the medium sensitivity setting, meaning that there will be an overall quicker response (i.e., faster alarm) whenever an OOB or EXITING condition is detected with the medium sensitivity setting FIG. 11 is a table showing a typical set of high sensitivity bed exit logic rules, in priority order from top to bottom, and assuming a debounced data set. The most significant difference between the high sensitivity and medium sensitivity settings is that an additional EXITING condition is established with the high sensitivity setting. This condition occurs when all the sensors in zone 1 are open for the applicable debounce time (rule No. 1), indicating a patient who is in bed but sitting up, or who has raised his shoulders or back off the surface of the bed. This setting is useful for a patient who is not allowed to sit up in bed. It also provides an even earlier notification of bed exit attempts. In addition, since the debounce times used are even shorter with the high sensitivity setting, an even quicker response and a faster alarm activation will occur.

The logic rules shown in FIGS. 9-11 are examples of logic rules which are especially well suited for use with the present invention. It will be appreciated, however, that variations in the logic rules may be possible in some embodiments, especially where the number and/or location of the sensors is varied.

In addition to activating the bed exit alarms, the bed exit detection system also is advantageously used, in some embodiments, as part of the vital signs monitoring system to enable the vital signs alarm only when a patient is determined to be present in the bed. This function is performed whether the bed exit alarm is enabled or not.

For example, when the bed exit sensors 36 detect that a patient is out of bed or is exiting the bed, the bed exit alarm will be sounded (if set) and the processor will automatically disable the physiologic alarms. If there are no active alarms before the patient tries to leave the bed, the physiologic alarms will be suspended and the display 20 (when activated) on the bedside unit 12 will provide a visual indication (e.g., display "out of bed" and will display dashes instead of vital signs data), until the patient is detected back in bed. This will help to eliminate false physiologic alarms due to an empty bed, rather than an actual physiological condition of the patient. On the other hand, if any physiologic alerts are active before the patient tries to exit the bed, those alerts are continued (latching) even after the patient leaves the bed in order to inform the nurse or other caregiver of the patient's condition before the bed exit event occurs.

In most embodiments, the bed exit alarm is non-latching, meaning that if the patient responds to the warning and gets back into bed, the bed exit alarm (if set) will be immediately silenced and reset. The physiologic alerts will be re-armed after a short (e.g., ten second) delay corresponding to the IB debounce time. The IB debounce time will change, depending on which sensitivity setting is active. If the bed exit alarm is turned off (such as for a patient with no bed exit restrictions), a ten-second delay (debounce time) is typically used before the physiologic alerts are re-armed by the processor.

Referring now to FIG. 12, there is shown an electrical schematic diagram of at least one example of electrical circuitry suitable for use in connecting a single zone of bed exit sensors 36 to the processor. In this figure, the seven switches in the zone are labeled as S1 through S7, respectively, for ease of identification.

An output signal from the signal processor is directed over line P1 and applied as a common input to one side of each switch in the zone. The signal received on line P1 is communicated to the opposite side of a switch as an output signal when the switch is closed due to the weight of a patient's body. These output signals are directed over different output lines P2 through P5, depending on which switch is activated. Thus, the two switches in section a (S1 and S7) are connected in parallel to output line P5. The two switches in section b (S2 and S6) are connected in parallel to output line P4. The two switches in section c (S3 and S5) are connected in parallel to output line P3. The switch in section d (S4) is connected to output line P2. Each output line P2-P5 is connected to a different input channel of the processor. By continually monitoring the signals on each output line, the processor can determine whether the switches in the corresponding zones and sections are open or closed. Various sampling rates can be used by the bed exit software, but in at least one aspect of the invention, the sampling rate of the bed exit signal is eight samples per second.

As previously noted, both the heart rate and respiration rate sensors (PDVF) 32 and the bed exit sensors (membrane switches) 36 are advantageously integrated with a coverlet 50 adapted for use with a typical hospital bed mattress. A typical hospital bed coverlet 50 includes a top portion above, and a bottom portion below, a mattress core. In most cases, the coverlet is replaceable and is closed around the core with a zipper (not shown) or similar arrangement on at least one side of the mattress. Coverlets generally are made of a waterproof material, such as urethane coated fabric or butyl coated fabric.

In the context of the present invention, the coverlet 50 is designed to cover the existing mattress, either by placement over an existing mattress coverlet or as a replacement for the existing mattress coverlet directly over the mattress core and to anchor the sensor array relative to the mattress. The coverlet also is designed to contain all the wiring and electronics necessary to condition and transmit signals from the sensor array 14 to the bedside unit 12 for monitoring.

Any number of methods may be used for mounting the piezoelectric films 32 and pressure switches 36 onto the coverlet 50. In one embodiment, for example, the piezoelectric films 32 and pressure switches 36 are attached by adhesive to a polyurethane substrate or carrier sheet 52, which is in turn bonded to the underside of the top surface of the coverlet 50 by RF welding or other suitable methods (FIGS. 2 and 3). The wiring for communicating signals from the sensors 32, 36 is advantageously run along an inner edge of the coverlet 50 inside a wire harness pocket to a box (not shown) at the head end of the coverlet containing the signal conditioning circuitry for the piezoelectric films 32.

By integrating the sensors array with a coverlet 50 in the manner described, the sensors are maintained in a fixed position and placed in defined locations on the bed surface once the coverlet is attached to the mattress.

In one embodiment, the pre-processor circuitry 13 for the pressure sensor array also is housed in the box at the head end of the coverlet 50. In one form, the pre-processor 13 includes a multi-channel CPLD, which samples the signals from the pressure sensors and then multiplexes and sends the signals to the processor in the bedside unit 12, where the logic rules are applied.

The sensor array can be made in any suitable size or shape. In one embodiment, for example, the heart rate and respiration rate sensors 32 can be arranged to cover the entire width of the mattress surface up to several inches from each side of the mattress. In addition, the heart rate and respiration rate sensors 32 can be arranged to cover the entire chest area of the mattress, including the area about twenty inches to forty inches from the head of the mattress. Typical dimensions for each PDVF sensor strip 32 are about twenty-three inches long by about three-quarter inches wide, with a spacing of about four to five inches (or 4½ inches) between each adjacent film in the array.

The bed exit switches 36 can be arranged to cover the area of the mattress from about twenty inches to sixty inches from the head of the mattress. Typical dimensions for each bed exit switch zone (1, 21, 22, 23, 3) are about twenty-eight to thirty-two inches long by about one and a half to two inches wide, with a spacing of about four to five inches between each switch 36 in a zone, center-to-center. In one embodiment, the spacing between zones 21, 22, 23 in the hip area of the bed is about four and a half inches, with the zone 1 in the mid-back area of the bed being placed about twenty-six inches from the head end of the bed, and the zone 3 in the mid-leg area of the bed being placed about fifty-six inches from the head end of the bed, or about twenty-eight inches from the foot end of a typical three foot by seven foot hospital bed. A typical spacing between zone 1 in the mid-back area and the uppermost zone 21 in the hip area of the bed is about fourteen inches, while a typical spacing between zone 3 in the mid-leg area of the bed and the lower most zone 23 in the hip area of the bed is about ten inches. All of these dimensions can be varied somewhat to suit particular needs.

The pressure switches 36 are chosen to have a pressure threshold suitable for a wide patient population. While a variety of different thresholds can be used, a threshold of <11 mm Hg is approximate, and 3-6 mm Hg is especially well suited for use with the present invention. The switches 36 also may be vented, in any suitable manner, if desired, to improve reliability and allow for more consistent performance.

From the foregoing, it will be appreciated that the bed exit detection of the present invention provides for accurate and reliable detection of when a patient on bed exit restrictions in a hospital, nursing home, or other healthcare institution, is in bed, is out of bed, or is actively attempting to exit the bed. The system is simple and easy to use, can be customized for individual patients, and can be easily retrofit to an existing hospital bed. Significantly, the system is capable of being integrated into a vital signs monitoring system to provide more complete and comprehensive monitoring of patient conditions with a single monitoring system, enabling the hospital or other healthcare facility to more effectively utilize limited resources and clinical staff, while improving overall clinical outcomes and the delivery of healthcare services.

In alternative embodiments, it will be appreciated that the bed exit detection system of the present invention can be adapted for use as a monitor system to detect a patient exiting from a chair, wheel chair, or other patient support structure. For example, the bed exit sensors of the present invention can be installed in one or more of the seat, seatback, headrest, or footrest areas of a chair or wheel chair. One or more sensor zones of the type described can be provided in each such location. The sensors on the chair transmit information about the patient's position to a central processor built into the chair via hardwiring or to a remote central processor using wireless technology.

While several particular forms of the invention have been illustrated and described, it will be apparent that various modifications can be made without departing from the spirit and scope of the invention.

We claim:

1. Bed patient monitoring apparatus, comprising:
   a plurality of discrete pressure sensors for installation at multiple locations along the length and width of a bed proximate areas occupied by the torso, hips and leg portions of a patient reclining on the bed for detecting the presence thereon and absence thereof of the patient's anatomy;
   a first defined set of sensor state combinations indicating the presence of a patient in a central portion of the bed;
   a second defined set of sensor state combinations indicating that the patient is in a location on the bed wherein the patient is approaching exiting the bed at the side of the bed;
   a third defined set of sensor state combinations indicating that the patient is in a location on the bed wherein the patient is approaching exiting near the foot of the bed;
   a fourth defined set of sensor state combinations indicating the absence of the patient from the bed, said fourth defined set of sensor state combinations differing from said second and third defined sets of sensor state combinations;
   a signal processor in communication with the sensors for receiving electrical signals from the sensors indicative of the sensor states and for determining whether the sensor states are in said first, second, third or fourth set of sensor state combinations; and an alarm processor in communication with the signal processor configured to produce one or more alarm indications when the alarm processor determines that the sensor states have remained within said second or third set of sensor state combinations for a continuous, predetermined minimum period of time and when the alarm processor determines that the sensor states have remained within said fourth set of sensor state combinations for a continuous predetermined minimum period of time, the second and third sets of sensor state combinations having a different predetermined minimum period of time than the fourth set of sensor state combinations.

2. The apparatus of claim 1, wherein said pressure sensors comprise membrane switches.

3. The apparatus of claim 2, wherein said membrane switches are vented.

4. The apparatus of claim 1, wherein said pressure sensors are arranged for installation in a series of zones, each zone comprising a plurality of discrete pressure sensors arranged in one or more rows extending laterally across the width of the bed, a first row being provided in said mid-back area of the bed, three additional rows being provided in said hip area of the bed, and a fifth row being provided in said mid-leg area of the bed, each of said rows being parallel to the other rows.

5. The apparatus of claim 4, wherein each row includes at least seven pressure sensors placed side-by-side across the width of the bed.

6. The apparatus of claim 4, wherein adjacent pressure sensors at the ends of one or more rows are electrically shorted together to reduce the number of electrical signals received by the processor and to produce variable signal resolution along the row.

7. The apparatus of claim 1, wherein the pressure sensors are arranged for installation in a series of rows extending symmetrically across the width of the bed with respect to the centerline of the bed, the corresponding sensors in each row on opposite sides of the centerline being connected in parallel, whereby the same electrical signal is provided to the signal processor by each of said corresponding sensors.

8. The apparatus of claim 7, further comprising a processor having a plurality of input channels, with each pressure sensor being connected to a different input channel except for the pressure sensors connected in parallel with each other, which are connected to the same input channel.

9. The apparatus of claim 1, further comprising a fifth defined set of sensor state combinations differing from said second and third sets of sensor state combinations indicating that the patient is attempting to sit up in bed, wherein an alarm indication is provided when the sensor states remain in said fifth defined set of sensor state combinations for a continuous, predetermined minimum period of time.

10. The apparatus of claim 1, further comprising a sixth defined set of sensor state combinations differing from said second and third sets of sensor state combinations indicating that the patient is sitting up in bed but has slumped down toward the foot of the bed, wherein an alarm indication is provided when the sensor states remain in said sixth defined set of sensor state combinations for a continuous, predetermined minimum period of time.

11. The apparatus of claim 1, wherein the predetermined minimum period of time is user selectable from a set of times stored in a memory accessible by the signal processor.

12. The apparatus of claim 1, wherein the predetermined minimum period of time is in the range of about one second to about ten seconds.

13. The apparatus of claim 1, further comprising a memory accessible by the signal processor, said memory containing a plurality of different sets of logic rules to be applied by the signal processor for determining whether the sensor states are in the first, second, third or fourth set of sensor state combinations.

14. The apparatus of claim 13, wherein a user interface is provided to enable a caregiver to select a particular set of logic rules from the logic rules contained in the memory to be applied by the signal processor for a given patient.

15. The apparatus of claim 13, wherein each different set of logic rules defines a different set of sensor state combinations for at least the second and third defined sets of sensor state combinations, whereby a different sensitivity is provided for detecting when the patient is approaching exiting the bed.

16. The apparatus of claim 1, wherein said first defined set of sensor state combinations requires at least two sensor activations in the mid-back area of the bed or at least four sensor activations in the hip area of the bed.

17. The apparatus of claim 1, wherein said second and third defined sets of sensor state combinations require at least one sensor activation near the sides or foot of the bed.

18. The apparatus of claim 1, wherein the pressure sensors are disposed in an array mounted on a removable mattress coverlet.

19. The apparatus of claim 1, further comprising a plurality of piezoelectric sensor films located in an array with said pressure sensors for sensing vital signs from the patient, at least some of said pressure sensors being disposed between said piezoelectric sensor films.

20. The apparatus of claim 19, wherein said first defined set of sensor state combinations further indicates the presence of a patient in communication with the piezoelectric sensor films.

21. The apparatus of claim 1, wherein said alarm indication comprises a pre-recorded voice announcement in the vicinity of the patient's bed warning the patient to return to the bed.

22. The apparatus of claim 21, wherein said voice announcement is pre-recorded in the language of the patient.

23. The apparatus of claim 1, further comprising a nurse call interface for interconnecting the processor to a nurse call system, wherein said alarm indication comprises transmitting an alarm signal over said nurse call system.

24. The apparatus of claim 1, wherein said alarm is selectively enabled and disabled by a user.

25. The apparatus of claim 1, further comprising a plurality of piezoelectric sensors for installation on the bed at different locations adjacent at least some of said pressure sensors for sensing vital signs from the patient, said processor being in communication with said piezoelectric sensors for receiving electrical signals from the piezoelectric sensors and for determining vital signs data pertaining to the patient based on said signals, wherein the alarm processor is configured to provide a physiological alarm indication when the vital signs data are determined to satisfy one or more alarm conditions; and a nurse call interface in communication with the alarm processor and with an existing nurse call system for communicating said vital signs alarm indication to the nurse call system.

26. The apparatus of claim 25, wherein said pressure sensors and said piezoelectric sensors are commonly mounted on a removable mattress coverlet.

27. The apparatus of claim 1, wherein the plurality of pressure sensors includes pressure sensors of different sensitivity.

28. A method for monitoring at least one bed patient, comprising:
- providing a plurality of discrete pressure sensors on a bed surface at multiple locations along the length and width of the bed proximate areas occupied by the torso, hips and leg portions of a patient reclining on the bed for detecting the presence thereon and absence thereof of the patient's anatomy;
- placing a patient in the bed;
- sensing the presence of a patient in a central portion of the bed with a first defined set of sensor state combinations;
- sensing that the patient is in a location on the bed wherein the patient is approaching exiting at the side of the bed with a second defined set of sensor state combinations;
- sensing that the patient is in a location on the bed wherein the patient is approaching exiting at the foot of the bed with a third defined set of sensor state combinations;
- sensing the absence of the patient from the bed with a fourth defined set of sensor state combinations, said fourth defined set of sensor state combinations differing from said second and third defined sets of sensor state combinations;
- analyzing signals received from the sensors with a processor to determine whether the sensor states are in the first, second, third or fourth set of sensor state combinations; and
- providing an alarm when the sensor states remain within one of said second, third or fourth sets of sensor state combinations for a continuous, predetermined minimum period of time, the second and third sets of sensor state combinations having a different predetermined minimum period of time than the fourth set of sensor state combinations.

29. The method of claim 28, further comprising sensing that the patient is attempting to sit up in bed with a fifth defined set of sensor state combinations differing from said second and third sets of sensor state combinations, and providing an alarm indication when the sensor states remain in said fifth defined set of sensor state combinations for a continuous, predetermined minimum period of time.

30. The method of claim 28, further comprising sensing that the patient is sitting up in bed but has slumped down toward the foot of the bed with a sixth defined set of sensor state combinations differing from said second and third sets of sensor state combinations, and providing an alarm indication when the sensor states remain in said sixth defined set of sensor state combinations for a continuous, predetermined minimum period of time.

31. The method of claim 28, wherein the predetermined minimum period of time is user selectable.

32. The method of claim 28, wherein a different set of logic rules is applied for determining whether the sensors are in the first, second, third or fourth sets of sensor state combinations.

33. The method of claim 32, wherein the logic rules are user selectable.

34. Bed patient monitoring apparatus, comprising:
- a plurality of discrete pressure sensors for installation at multiple locations along the length and width of a bed proximate areas occupied by the torso and hip portions of a patient reclining on the bed for detecting the presence thereon and absence thereof of the patient's anatomy;
- a first defined set of sensor state combinations indicating the presence of a patient in a central portion of the bed;
- a second defined set of sensor state combinations indicating that the patient is in the bed in a position selected from the group consisting of sitting up in bed and slumping down in bed;
- a third defined set of sensor state combinations indicating the absence of the patient from the bed, said third defined set of sensor state combinations differing from said second defined set of sensor state combinations;
- a signal processor in communication with the sensors for receiving electrical signals from the sensors indicative of the sensor states and for determining whether the sensor states are in said first, second or third set of sensor state combinations; and
- an alarm processor in communication with the signal processor configured to produce one or more alarm indications when the alarm processor determines that the sensor states have remained within said second or third set of sensor state combinations for a continuous, predetermined minimum period of time, the second set of sensor state combinations having a different predetermined period of time than the third set of sensor state combinations.

35. Bed patient monitoring apparatus, comprising:
- a plurality of discrete pressure sensors for installation at multiple locations along the length and width of a bed proximate areas occupied by the mid-back, hips and leg portions of a patient reclining on the bed for detecting the presence thereon and absence thereof of the patient's anatomy;
- a first defined set of sensor state combinations indicating the presence of a patient in the bed;
- a second defined set of sensor state combinations indicating that the patient is approaching exiting the bed;
- a third defined set of sensor state combinations indicating the absence of the patient from the bed;
- a signal processor in communication with the sensors for receiving electrical signals from the sensors indicative of the sensor states and for determining whether the sensor states are in said first, second or third set of sensor state combinations;
- an alarm processor in communication with the signal processor configured to produce one or more alarm indications when the sensor states remain within one of said second or third set of sensor state combinations for a continuous, predetermined minimum period of time; and
- wherein said pressure sensors are arranged for installation in a series of zones, each zone comprising a plurality of discrete pressure sensors arranged in one or more rows extending laterally across the width of the bed, at least one row being provided in said mid-back area of the bed, and at least one row being provided in said hip area of the bed, the area between said row in the mid-back and hip areas being free of said pressure sensors.

* * * * *

UNITED STATES PATENT AND TRADEMARK OFFICE
CERTIFICATE OF CORRECTION

PATENT NO.        : 7,656,299 B2                                            Page 1 of 1
APPLICATION NO. : 11/624200
DATED             : February 2, 2010
INVENTOR(S)       : Gentry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this

Twenty-eighth Day of December, 2010

David J. Kappos
*Director of the United States Patent and Trademark Office*